(12) United States Patent
Platt et al.

(10) Patent No.: US 10,208,349 B2
(45) Date of Patent: Feb. 19, 2019

(54) LIPOCALIN 2 AS A BIOMARKER FOR IL-17 INHIBITOR THERAPY EFFICACY

(71) Applicant: UCB BIOPHARMA SPRL, Brussels (BE)

(72) Inventors: Adam Samuel Platt, Congleton (GB); Stephen Edward Rapecki, Slough (GB); Mara Fortunato, Saluggia (IT); David Robert Rainey, Slough (GB); Jon Leigh Rundle, Stotfold (GB); Paul Alfred Smith, Basel (CH); Gillian Sairfull Watt, Luton (GB)

(73) Assignee: UCB BIOPHARMA SPRL, Brussels (BE)

( * ) Notice: Subject to any disclaimer, the term of this patent is extended or adjusted under 35 U.S.C. 154(b) by 285 days.

(21) Appl. No.: 14/084,047

(22) Filed: Nov. 19, 2013

(65) Prior Publication Data

US 2014/0080134 A1 Mar. 20, 2014

Related U.S. Application Data

(63) Continuation of application No. 13/977,232, filed as application No. PCT/GB2012/000014 on Jan. 9, 2012, now abandoned.

(30) Foreign Application Priority Data

Jan. 7, 2011 (GB) .................................. 1100282.1

(51) Int. Cl.
*C12Q 1/68* (2018.01)
*G01N 33/68* (2006.01)
*C12Q 1/6883* (2018.01)
*C12Q 1/6886* (2018.01)

(52) U.S. Cl.
CPC ......... *C12Q 1/6883* (2013.01); *C12Q 1/6886* (2013.01); *G01N 33/6869* (2013.01); *G01N 33/6893* (2013.01); *C12Q 2600/106* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| 4,439,196 | A | 3/1984 | Higuchi |
| 4,447,224 | A | 5/1984 | DeCant, Jr. et al. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,596,556 | A | 6/1986 | Morrow et al. |
| 4,741,900 | A | 5/1988 | Alvarez et al. |
| 4,790,824 | A | 12/1988 | Morrow et al. |
| 4,941,880 | A | 7/1990 | Burns |
| 4,946,778 | A | 8/1990 | Ladner et al. |
| 4,980,286 | A | 12/1990 | Morgan et al. |
| 5,064,413 | A | 11/1991 | McKinnon et al. |
| 5,223,409 | A | 6/1993 | Ladner et al. |
| 5,312,335 | A | 5/1994 | McKinnon et al. |
| 5,383,851 | A | 1/1995 | McKinnon, Jr. et al. |
| 5,399,163 | A | 3/1995 | Peterson et al. |
| 5,403,484 | A | 4/1995 | Ladner et al. |
| 5,427,908 | A | 6/1995 | Dower et al. |
| 5,516,637 | A | 5/1996 | Huang et al. |
| 5,571,698 | A | 11/1996 | Ladner et al. |
| 5,580,717 | A | 12/1996 | Dower et al. |
| 5,585,089 | A | 12/1996 | Queen et al. |
| 5,658,727 | A | 8/1997 | Barbas et al. |
| 5,677,425 | A | 10/1997 | Bodmer et al. |
| 5,698,426 | A | 12/1997 | Huse |
| 5,733,743 | A | 3/1998 | Johnson et al. |
| 5,738,996 | A | 4/1998 | Hodges et al. |
| 5,750,753 | A | 5/1998 | Kimae et al. |
| 5,780,225 | A | 7/1998 | Wigler et al. |
| 5,807,683 | A | 9/1998 | Brenner |
| 5,821,047 | A | 10/1998 | Garrard et al. |
| 5,969,108 | A | 10/1999 | McCafferty et al. |
| 2008/0044423 | A1* | 2/2008 | Cochrane ............... C07K 14/54 424/139.1 |
| 2008/0219979 | A1* | 9/2008 | Tocker ............... C07K 16/2866 424/135.1 |

(Continued)

FOREIGN PATENT DOCUMENTS

| WO | WO-90/002809 A1 | 3/1990 |
| WO | WO-91/010737 A1 | 7/1991 |
| WO | WO-92/001047 A1 | 1/1992 |

(Continued)

OTHER PUBLICATIONS

Chao CC, Chen SJ, Adamopoulos IE, Davis N, Hong K, Vu A, Kwan S, Fayadat-Dilman L, Asio A, Bowman EP. Anti-IL-17A therapy protects against bone erosion in experimental models of rheumatoid arthritis. Autoimmunity. May 2011; 44(3):243-52. Epub Oct. 7, 2010.*

Hartgring SA, van Roon JA, Wenting-van Wijk M, Jacobs KM, Jahangier ZN, Willis CR, Bijlsma JW, Lafeber FP. Elevated expression of interleukin-7 receptor in inflamed joints mediates interleukin-7-induced immune activation in rheumatoid arthritis. Arthritis Rheum. Sep. 2009; 60(9):2595-605.*

Hu Y, Shen F, Crellin NK, Ouyang W. The IL-17 pathway as a major therapeutic target in autoimmune diseases. Ann N Y Acad Sci. Jan. 2011; 1217:60-76. Epub Dec. 13, 2010. Review.*

Ivanov S, Linde'n A. Interleukin-17 as a drug target in human disease. Trends Pharmacol Sci 2009; 30: 95-103.*

(Continued)

*Primary Examiner* — Aaron A Priest
*Assistant Examiner* — Olayinka A Oyeyemi
(74) *Attorney, Agent, or Firm* — Marshall, Gerstein & Borun LLP

(57) ABSTRACT

The present invention provides the use of lipocalin 2 (LCN2) as a biomarker for IL-17 mediated diseases and for monitoring the response of a patient to anti-IL-17 therapy.

6 Claims, 3 Drawing Sheets

(56) References Cited

U.S. PATENT DOCUMENTS

| | | | | |
|---|---|---|---|---|
| 2009/0305963 | A1* | 12/2009 | Sukhatme | A61K 38/164 514/15.1 |
| 2011/0212104 | A1* | 9/2011 | Beaumont | C07K 16/244 424/158.1 |

FOREIGN PATENT DOCUMENTS

| | | | | |
|---|---|---|---|---|
| WO | WO-92/002551 | A1 | 2/1992 | |
| WO | WO-92/018619 | A1 | 10/1992 | |
| WO | WO-92/022583 | A2 | 12/1992 | |
| WO | WO-93/008829 | A1 | 5/1993 | |
| WO | WO-93/011236 | A1 | 6/1993 | |
| WO | WO-95/015982 | A2 | 6/1995 | |
| WO | WO-95/020401 | A1 | 8/1995 | |
| WO | WO-98/025971 | A1 | 6/1998 | |
| WO | WO-99/015549 | A2 | 4/1999 | |
| WO | WO-02/058717 | A2 | 8/2002 | |
| WO | WO2005051422 | * | 6/2005 | A61K 39/395 |
| WO | WO-2006/013107 | A1 | 2/2006 | |
| WO | WO-2006/054059 | A1 | 5/2006 | |
| WO | WO-2006/125105 | A2 | 11/2006 | |
| WO | 20070057395 | A2 | 5/2007 | |
| WO | WO-2007/070750 | A1 | 6/2007 | |
| WO | WO-2007/076523 | A2 | 7/2007 | |
| WO | WO2007106769 | * | 9/2007 | |
| WO | WO-2007/149032 | A1 | 12/2007 | |
| WO | WO-2008/047134 | A2 | 4/2008 | |
| WO | WO-2009/040562 | A1 | 4/2009 | |
| WO | WO-2009/136286 | A2 | 11/2009 | |
| WO | WO-2010/025400 | A2 | 3/2010 | |
| WO | WO-2010/035012 | A1 | 4/2010 | |
| WO | WO-2010/062663 | A1 | 6/2010 | |
| WO | WO-2011/008609 | A1 | 1/2011 | |
| WO | WO-2011/030107 | A1 | 3/2011 | |
| WO | WO2011046958 | * | 4/2011 | C07K 16/28 |
| WO | WO-2011/061492 | A2 | 5/2011 | |

OTHER PUBLICATIONS

Lequerre T, Gauthier-Jauneau AC, Bansard C, Derambure C, Hiron M, et al. (2006) Gene profiling in white blood cells predicts infliximab responsiveness in rheumatoid arthritis. Arthritis Res Ther 8: R105" pp. 1-11.*

Lubberts E, Koenders MI, Oppers-Walgreen B, van den Bersselaar L, Coenen-de Roo CJ, Joosten LA, van den Berg WB. Treatment with a neutralizing anti-murine interleukin-17 antibody after the onset of collagen-induced arthritis reduces joint inflammation, cartilage destruction, and bone erosion. Arthritis Rheum. Feb. 2004; 50(2):650-9.*

Rioja I, Clayton CL, Graham SJ, Life PF, Dickson MC. Gene expression profiles in the rat streptococcal cell wall-induced arthritis model identified using microarray analysis. Arthritis Res Ther. 2005; 7(1):R101-17. Epub Nov. 19, 2004.*

Stuhlmuller B, Häupl T, Hernandez MM, Grützkau A, Kuban RJ, Tandon N, Voss JW, Salfeld J, Kinne RW, Burmester GR. CD11c as a transcriptional biomarker to predict response to anti-TNF monotherapy with adalimumab in patients with rheumatoid arthritis. Clin Pharmacol Ther. Mar. 2010; 87(3):311-21. Epub Dec. 23, 2009.*

Tsuzaka K, Itami Y, Takeuchi T, Shinozaki N, Morishita T. ADAMTS5 is a biomarker for prediction of response to infliximab in patients with rheumatoid arthritis. J Rheumatol. Jul. 2010; 37(7):1454-60. Epub Jun. 1, 2010.*

Yang XO, Chang SH, Park H, Nurieva R, Shah B, Acero L, Wang YH, Schluns KS, Broaddus RR, Zhu Z, Dong C. Regulation of inflammatory responses by IL-17F. J Exp Med. May 12, 2008; 205(5):1063-75. Epub Apr. 14, 2008.*

Chabaud M, Durand JM, Buchs N, Fossiez F, Page G, Frappart L, Miossec P. Human interleukin-17: A T cell-derived proinflammatory cytokine produced by the rheumatoid synovium. Arthritis Rheum. May 1999; 42(5):963-70.*

Chabaud M, Garnero P, Dayer JM, Guerne PA, Fossiez F, Miossec P. Contribution of interleukin 17 to synovium matrix destruction in rheumatoid arthritis. Cytokine. Jul. 2000; 12(7):1092-9.*

Genovese MC, Van den Bosch F, Roberson SA, Bojin S, Biagini IM, Ryan P, Sloan-Lancaster J. LY2439821, a humanized anti-interleukin-17 monoclonal antibody, in the treatment of patients with rheumatoid arthritis: A phase I randomized, double-blind, placebo-controlled, proof-of-concept study. Arthritis Rheum. Apr. 2010; 62(4):929-39.*

Miossec P. IL-17 and Th17 cells in human inflammatory diseases. Microbes Infect. Apr. 2009; 11(5):625-30. Epub Apr. 14, 2009.*

Nakahara H, Song J, Sugimoto M, Hagihara K, Kishimoto T, Yoshizaki K, Nishimoto N. Anti-interleukin-6 receptor antibody therapy reduces vascular endothelial growth factor production in rheumatoid arthritis. Arthritis Rheum. Jun. 2003; 48(6):1521-9. (Year: 2003).*

Baker, D. et al., Induction of chronic relapsing experimental allergic encephalomyelitis in Biozzi mice, Journal of Neuroimmunology, 1990, pp. 261-270, vol. 17, Elsevier Science Publishers B.V.

Bollard, Catherine M. et al., Adapting a transforming growth factor β-related tumor protection strategy to enhance antitumor immunity, Gene Therapy, May 1, 2002, pp. 3179-3188, vol. 99, No. 9, The American Society of Hematology.

Carrel, Thomas et al., A Novel Procedure for the Systhesis of Libraries Containing Small Organic Molecules**, Angewandte Chemie International Edition, 1994, pp. 2059-2062, vol. 33, No. 20, VCH Verlagsgesellschaft mbH, D-69451 Weinheim.

Carell, Thomas et al., A Solution-Phase Screening Procedure for the Isolation of Active Compunds from a Library of Molecules**, Angewandte Chemie International Edition, 1994, pp. 2061-2064, vol. 33, No. 20, VCH Verlagsgesellschaft mbH, D-69451 Weinheim.

Cho, Charles Y., An Unnatural Biopolymer, Science, Sep. 3, 1993, pp. 1303-1306, vol. 261.

Chung, Doo Ryeon et al., CD4+T Cells Regulate Surgical and Postinfectious Adhesion Formation, Journal of Experimental Medicine, Jun. 3, 1992, pp. 1471-1478, vol. 195, No. 11, The Rockefeller University Press.

Cull, Millard G. et al., Screening for receptor ligands using large libraries of peptides linked to the C terminus of the lac repressor, Proceedings of the National Academy of Sciences, Biochemistry, Mar. 1992, pp. 1865-1869, vol. 89, USA.

Cwirla, Teven E. et al., Peptides on phage: A vast library for identifying ligands, Proceedings of the National Academy of Sciences, Biochemistry, Aug. 1990, pp. 6378-6382, vol. 87, USA.

Devarajan, Prasad, Emerging Biomarkers of Acute Kidney Injury, Early Diagnosis and Prevention of AKI, 2007, pp. 203-212, vol. 156.

Devlin, James J. et al., Random Petptide Libraries: A Source of Specific Protein Binding Molecules, Department of Molecular Biology, Science, pp. 404-406, vol. 249, Emeryville, CA.

DeWitt, Sheila Hobbs, "Diversomers": An approach to nonpeptide, nonoligomeric chemical diversity, Proceedings of the National Academy of Sciences, Chemistry, Aug. 1993, pp. 6909-6913, vol. 90, USA.

Dumont, Francis J., IL-17 cytkine/receptor families: emergine targets for the modulation of inflammatory responses, Monthly focus: Biologicals, Immunologicals and Drug Delivery, 2003, pp. 287-303, Ashley Publications, Ltd.

Erb, Eric et al., Recursive deconvolution of combinatorial chemical libraries, Proceeding of the National Academy of Sciences, Chemistry, Nov. 1994, pp. 11422-11426, vol. 91, USA.

Felici, Franco et al., Selectionof Antibody Ligands from a Large Library of Oligopeptides Expressed on Multivalent Exposition Vector, Journal of Molecular Biology, 1991, pp. 301-310, vol. 222, Academic Press Limited.

Ferretti, Stephane et al., IL-17, Produced by Lymphocytes and Neutrophils, Is Necessary for Lipopolysaccharide-Induced Airway Neutrophilia: IL-15 as a Possible Trigger, The Journal of Immunology, 2003, pp. 2106-2112, The American Association of Immunologists, Inc.

Flo, Trude H. et al., Lipocalin 2 mediactes an innate immune response to bacterial infection by sequestrating iron, Nature, Dec. 16, 2004, pp. 917-921, vol. 432.

(56) References Cited

OTHER PUBLICATIONS

Fodor, Stephen P. et al., Multiplexed biochemical assays with biological chips, Nature, Product Review, Aug. 5, 1993, pp. 555-556, Nature Publishing Group.

Fossiez, Francois et al., Interleukin-17, International Reviews of Immunology, 1998, pp. 541-551, vol. 16, OPA (overseas Publishing Association).

Gaffen, Sarah L., An overview of IL-17 function and signaling, Cytokine, 2008, pp. 402-407, vol. 43, Elsevier Ltd.

Gallop, Mark A. et al., Applications of Combinatorial Technologies to Drug Discovery. 1. Background and Peptide Combinatorial Libraries, Journal of Medicinal Chemistry, Apr. 29, 1994, pp. 1233-1251, vol. 37, No. 9, American Chemical Society.

Hoshida, Tohru et al., Gene Therapy for Pancreatic Cancer Using an Adenovirus Vector Encoding Soluble flt-1 Vascular Endothelial Growth Factor Receptor, Pancreas, 2002, pp. 111-121, vol. 25, Lippincott & Wilkins, Inc., Philadelphia.

Houghten, R. A. et al., The Use of Synthetic Peptide Combinatorial Libraries for the Identification of Bioactive Peptides, BioTechniques, BioFeature, 1992, pp. 412-421, vol. 13, No. 3.

Ikuno, Yasushi et al., An In Vivo Gene Therapy Approach for Experimental Proliferative Vitreoretinopathy Using the Truncated Platelet-Derived Growth Factor α Receptor, Investigative Opthalmology & Visual Science, Jul. 2002, vol. 43, No. 7, Association for Research in Vision and Opthalmology.

Jacoby, C. Fraefel et al., Hybrid vectors: a new generation of virus-based vectors designed to control the cellular fate of delivered genes, Editorial, Gene Therapy, 1997, pp. 1281-1283, vol. 4, Stockton Press.

Jelinsky, Scott A. et al., Exploiting genotypic differences to identify genes important for EAE development, Journal of the Neurological Sciences, 2005, pp. 81-93, vol. 239, Elsevier B.V.

Kochanek, Stefan, High-Capacity Adenoviral Vectors for Gene Transfer and Somatic Gene Therapy, Human Gene Therapy, Oct. 10, 1999, pp. 2451-2459, vol. 10, Mary Ann Liebert, Inc., Center for Molecular Medicine, (ZMMK), University of Cologne, D-50931, Cologne, Germany.

Köhler, G. et al., Continuous cultures of fused cells secreting antibody of predefined specificity, Nature, Aug. 7, 1975, pp. 495-497, vol. 256, nature Publishing Group.

Korn, Thomas et al., IL-17 and Th-17 Cells, Annual Review of Immunology, 2009, pp. 485-517, vol. 27, Annual Reviews.

Kuestner, Rolf E. et al., Identification of the IL-17 Receptor Related Molecule IL-17RC as the Receptor for IL-17F, The Journal of Immunology, 2007, pp. 5462-5473, The American Association of Immunologists, Inc.

Lam, Kit S., Application of combinatorial library methods in cancer research and drug discovery, Anti-Cancer Drug Design, 1997, pp. 145-167, vol. 12, Oxford University Press.

Lam, Kit S., et al., A new type of synthetic peptide library for identifying ligand-binding activity, Nature, Letters to Nature, pp. 7 Nov. 1991, vol. 354, Nature Publishing Group.

Lee, Eun Jig et al., Adenovirus-directed Expression of Dominant Negative Estrogen Receptor Induces Apoptosis in Breast Cancel Cells and Regression of Tumors in Nude Mice, Molecular Medicine, 2001, pp. 773-782, vol. 7, No. 11, The Picower Institute Press.

Lim, Ratana et al., Neutrophol Gelatinase-assiciated lipocalin (NGAL) an early-screening biomarker for ovarian cancer: NGAL is associated with epidermal growth factor-induced epithelio-mesenchymal transition, International Journal of Cance, 2007, pp. 2426-2434, vol. 120, Wiley-Liss, Inc.

Lubberts, Erik et al., IL-1-Independent Role of IL-17 in Synovial Inflammation and Joint Destruction During Collagen-Induced Arthritis, The Journal of Immunology, 2001, pp. 1004-1013, The American Association of Immunologists.

Miller, A. Dusty et al., Use of Retroviral Vectors for Gene Transfer and Expression, Methods in Enzymology, 1993, pp. 581-599, vol. 217, Academic Press, Inc.

Milstein, C. et al., Hybrid hybridomas and their use in immunohistochemistry, Nature, Letters to Nature, Oct. 1983, pp. 837-840, vol. 305, No. 6, Macmillan Journals, Ltd.

Moseley, T. A. et al., Interleukin-17 family and IL-17 receptors, Cytokine & Growth Factor Reviews, 2003, pp. 155-174, vol. 14, Elsevier Science Ltd.

Persic, Lidija et al., An integrated vector system for the eukaryotic expression of antibodies or their fragments after selection from phage display libraries, Gene, 1997, pp. 9-18, vol. 187, Elsevier Science B.V.

Reynolds, Paul N. et al., Chimeric viral vectors—the best of both worlds?, Molecular Medicine Today, Jan. 1999, pp. 25-31, Elsevier Science.

Robbins, Paul D. et al., Viral Vectors for Gene Therapy, Pharmacology & Therapeutics, 1998, pp. 35-47, vol. 80, No. 1, Elsevier Science Inc.

Schmidt-Ott, Kai M. et al., Dual Action of Neutrophil Gelatinase-Associted Lipocalin, American Society of Nephrology, Frontiers in Nephrology, 2007, pp. 407-413, vol. 18, American Society of Nephrology.

Schoonjans, Reinhilde et al., A new model for intermediate molecular weight recombinant bispecific and trispecific antibodies by efficient heterodimerization of single chain variable domains through fusion to a Fab-chain, Biomolecular Engineering, 2001, pp. 193-202, vol. 17 Elsevier Science B.V.

Scott, Jamie K. et al., Searching for Peptide Ligands with an Epitope Library, Science, Jul. 27, 1990, pp. 386-390, vol. 249.

Shen, Fang et al., Identification od Common Transcriptional Regulatory Elements in Interleukin-17 target Genes, The Journal of Biological Chemistry, Aug. 25, 2006, pp. 24138-24148, vol. 281, No. 34, The American Society for Biochemistry and Molecular Biology, inc.

Toy, Dean et al., Cutting Edge: Interleukin 17 Signals through a Heteromeric Receptor Complex, The Journal of Immunology, 2006, pp. 36-39, The American Association of Immunologists, Inc.

Traunecker, André et al., Bispecific single chain molecules (Janusins) target cytotoxic lymphocytes on HIV infected cells, The EMBO Journal, 1991, pp. 3655-3659, vol. 10, No. 12, Oxford University Press.

Wang, Yu et al., Lipocalin-2 Is an Inflammatory Marker Closely Associated with Obesity, Insulin Resistance, and Hyperglycemia in Humans, Clinical Chemistry, 2007, pp. 34-41, vol. 53, No. 1, Proteomics and Protein Markers.

Wright, Jill F. et al., The Human IL-17F/IL-17A Heterodimeric Cytokine Signals theough the IL-17RA/IL-17RC Receptor Complex, The Journal of Immunology, 2008, pp. 2799-2805, The American Association of Immunologies, Inc.

Wu, George Y. et al., Receptor-mediated in Vitro Gene Transformation by a Soluble DNA Carrier System, The Journal of Biological Chemistry, 1987, pp. 4429-4432, vol. 262, No. 10, The American Society of Biological Chemists, Inc.

Xu, S. Y. et al., The development of an assay for human neutrophil lipocalin (HNL)—to be used as a specific marker of neutrophil activity in vivo and vitro, Journal of Immunological Methods, 1994, pp. 245-252, vol. 171, Elsevier Science B.V.

Xu, Shengyuan et al., Lipocalins as biochemical markers of disease, Biochimica et Biophysica Acta, 2000, pp. 298-307, vol. 1482, Elsevier Science B.V.

Yao, Zhengbin et al., Human IL-17: A Novel Cytkine Derived from T Cells, The Journal of Immunology, Cutting Edge, 1995, The American Association of Immunologists.

Yao, Zhengbin et al., Molecular Characterization of the Human Interleukin (IL)-17 Receptor, Cytokine, Nov. 1997, pp. 794-800, vol. 9, No. 11, Academic Press Limited.

Zuckermann, Ronald N. et al., Discovery of Nanomolar Ligands for 7-Transmembrane G-Protein-Coupled Receptors from Diverse N-(Substituted)glycine Peptoid Library, Journal of Medicinal Chemistry, 1994, pp. 2678-2685, vol. 37, American Chemical Society.

Ames, R.S., et al., "Conversion of murine Fabs isolated from a combinatorial phage display library to full length immunoglobulins," J. Immunol. Methods, vol. 184, No. 2, pp. 177-186, 1995.

(56) References Cited

OTHER PUBLICATIONS

Babcook, J., et al., "A novel strategy for generating monoclonal antibodies from single, isolated lymphocytes producing antibodies of defined specificities," Proc. Natl. Acad. Sci. USA, vol. 93, No. 15, pp. 7843-7848, 1996.

Brinkman, U., et al., "Phage Display of Disulfide-Stabilized FV Fragments," J. Immunol. Methods, vol. 182, No. 1, pp. 41-50, 1995.

Brodmerkel, C. et al., "The Skin and Circulating Immune Profile of Therapeutic IL-12/23 Blockade in Psoriasis Patients Treated with Ustekinumab," Clin. Immunol., vol. 131, pp. S5, 2009.

Burton, et al., "Human Antibodies from Combinatorial Libraries," Advances in Immunology, vol. 57, pp. 191-280, 1994.

Cole, S.P.C., et al., "The EBV-hybridoma technique and its application to human lung cancer," Monoclonal Antibodies and Cancer Therapy, pp. 77-96, Alan R. Liss, Inc., 1985.

De Kok et al., Real-time Quantification of Human Telomerase Reverse TranscriptasemRNA in Tumors and Health Tissues, Clin. Chem., vol. 46, No. 3, pp. 313-318, 2000.

Guttman-Yassky, E. et al., "Low Expression of the IL-23/Th17 Pathway in Atopic Dermatitis Compared to Psoriasis," J. Immunol., vol. 181, No. 10, pp. 7420-7427, 2008.

Holliger, P., and Hudson, P.J., "Engineered antibody fragments and the rise of single domains," Nature Biotechnology, vol. 23, No. 9, pp. 1126-1136, 2005.

International Search Report and Written Opinion based on PCT/GB2012/000014 dated May 23, 2012.

Kettleborough, C.A., et al., "Isolation of tumor cell-specific single-chain Fv from immunized mice using phage-antibody libraries and the reconstruction of whole antibodies from these antibody fragments," Eur. J. Immunol., vol. 24, No. 4, pp. 952-958, 1994.

Kozbor, D., et al., "The production of monoclonal antibodies from human lymphocytes", Immunology Today, vol. 4, No. 3, pp. 72-79, 1983.

Ratana et al., "Neutrophil gelatinase-associated lipocalin (NGAL) an early-screening biomarker for ovarian cancer: NGAL is associated with epidermal growth factor-induced epithelio-mesenchymal transition," International Journal of Cancer, vol. 120, No. 11, pp. 2426-2434, 2007.

Shen, F. et al., "Cytokines Link Osteoblasts and Inflammation: Microarray Analysis of Interleukin-17- and TNF-a-Induced Genes in Bone Cells," Journal of Leukocyte Biology, vol. 77, No. 3, pp. 388-399, 2005.

Verma, R., et al., "Antibody engineering: comparison of bacterial, yeast, insect and mammalian expression systems," Journal of Immunological Methods, vol. 216, Nos. 1-2, pp. 165-181, 1998.

* cited by examiner

LIPOCALIN 2 AS A BIOMARKER FOR IL-17 INHIBITOR THERAPY EFFICACY

CROSS REFERENCE TO RELATED APPLICATIONS

This application is a continuation of U.S. application Ser. No. 13/977,232, filed Jan. 9, 2012, which is the national phase of International Application No. PCT/GB2012/000014, filed on Jan. 9, 2012, which claims priority to Great Britain Application No. 1100282.1, filed Jan. 7, 2011, the entire contents of each of which are fully incorporated herein by reference.

BACKGROUND OF THE INVENTION

The present invention relates generally to the use of lipocalin 2 as a biomarker for IL-17 mediated diseases and for monitoring the response of a patient to anti-IL-17 therapy.

Interleukin 17 (IL-17), also known as CTLA-8 or IL-17A, is a pro-inflammatory cytokine which stimulates the secretion of a wide range of other cytokines from various non-immune cells. IL-17 is capable of inducing the secretion of IL-6, IL-8, PGE2, MCP-1 and G-CSF by adherent cells like fibroblasts, keratinocytes, epithelial and endothelial cells and is also able to induce ICAM-1 surface expression, proliferation of T cells, and growth and differentiation of CD34+ human progenitors into neutrophils when cocultured in presence of irradiated fibroblasts (Fossiez et al., 1998, Int. Rev. Immunol. 16, 541-551). IL-17 is predominantly produced by activated memory T cells and acts by binding to a ubiquitously distributed cell surface receptor (IL-17R) (Yao et al., 1997, Cytokine, 9, 794-800). It may also act through binding to a complex of IL-17RA and IL-17RC (Toy et al., 2006, J. Immunol. 177(11); 36-39). A number of homologues of IL-17 have been identified which have both similar and distinct roles in regulating inflammatory responses. For a review of IL-17 cytokine/receptor families see Dumont, 2003, Expert Opin. Ther. Patents, 13, 287-303.

The most closely related homologue is IL-17F (ML-1), which shares approximately 55% amino acid sequence homology with IL-17A (Moseley et al., 2003, *Cytokine Growth Factor Rev.* 14: 155-174). IL-17A and IL-17F are expressed by the recently defined autoimmune related subset of T helper cells, Th17, that also express IL-21 and IL-22 signature cytokines (Korn et al., 2009, *Annu. Rev. Immunol.* 27:485-517.: 485-517). IL-17A and IL-17F are expressed as homodimers, but may also be expressed as the IL-17A/F heterodimer (Wright et al. 2008, *J. Immunol.* 181: 2799-2805). IL-17A and F signal through the receptors IL-17R, IL-17RC or an IL-17RA/RC receptor complex (Gaffen 2008, *Cytokine.* 43: 402-407). Both IL-17A and IL-17F have been associated with a number of autoimmune diseases.

IL-17 may contribute to a number of diseases mediated by abnormal immune responses, such as rheumatoid arthritis, multiple sclerosis and air-way inflammation, as well as organ transplant rejection and antitumour immunity. Inhibitors of IL-17 activity are well known in the art, for example an IL-17R:Fc fusion protein was used to demonstrate the role of IL-17 in collagen-induced arthritis (Lubberts et al., J. Immunol. 2001, 167, 1004-1013), neutralising polyclonal antibodies have been used to reduce peritoneal adhesion formation (Chung et al., 2002, J. Exp. Med., 195, 1471-1478) and a neutralising antibody to IL-17 was used to demonstrate the role of IL-17 in Experimental Autoimmune Encephalomyelitis, a murine model of MS (WO2005/051422). Numerous neutralising anti-IL-17A antibodies have been described, see for example those described in WO2006/054059, WO2006/013107, WO2007070750 and WO2007149032. Antibodies which bind both IL-17A and IL-17F have also been described, see for example, WO2007/106769, WO2008/047134, WO2009/136286 and WO2010/025400.

The role of biomarkers is becoming increasingly important in the clinical development of therapeutics. A biomarker can be an indicator of normal biological processes, disease processes or pharmacological responses to therapeutic intervention. Their role ranges from stratifying the patient population in helping to identify responders versus non-responders, to determining the dosing and efficacy of the therapeutic. Accordingly, biomarkers can be valuable tools in making better decisions that will reduce the cost for drug development and target therapies to the most suitable patient population.

Lipocalins are small secreted proteins with a common tertiary structure that binds lipophilic molecules such as prostaglandins and cholesterol and some are known to be biomarkers of certain diseases (Xu and Venge, 2000, Biochimica et Biophysica Acta, 1482, 298-307). One such lipocalin is lipocalin 2 (LCN2), also known as 24p3 or neutrophil gelatinase-associated lipocalin (NGAL) which is a 25 kDa secretory glycoprotein that was originally identified in mouse kidney cells and human neutrophil granules. LCN2 has been demonstrated to be a biomarker for early detection of various renal injuries, obesity and cancer (see for example, Devarajan, 2007, Contributions to Nephrology, 156, 203-212; Wang et al., 2007, Clinical Chemistry, 53, 34-41; Ratana et al, 2007, International Journal of Cancer, 120 (11), 2426-34). LCN2 gene expression has been shown to be upregulated in Experimental Autoimmune Encephalomyelitis, a murine model of MS (Jelinsky et al., 2005, Journal of Neurological Sciences, 239, 81-93). IL-17 has been demonstrated to be involved in the transcriptional regulation of LCN2 in vitro via NF-κB and C/EBP (Shen et al., 2006, Journal of Biological Chemistry, 281, 34, 24138-24148; Shen et al., 2005, Journal of Leukocyte Biology, 77, 388-399). Whether IL-17 regulates LCN2 in vivo is not known.

The present invention demonstrates that LCN2 can serve as a biomarker for IL-17 mediated diseases and for anti-IL-17 therapy. Specifically we have been able to demonstrate that a neutralising anti-IL-17 antibody reduces LCN2 expression in an animal model of MS. Hence, in one embodiment the present invention provides a method of monitoring the response of a subject to a medicament comprising an IL-17 inhibitor, wherein the level of expression of lipocalin 2 in a test sample of a body fluid or tissue obtained from the subject is assessed before and after administration of said medicament and wherein the level of expression of lipocalin 2 after administration of the medicament is compared to the level of expression of lipocalin 2 prior to administration of the medicament. The levels of expression of lipocalin 2 in the subject before and after administration of the medicament are compared in order to determine the efficacy of the IL-17 inhibitor therapy.

In the present application the use of the term 'IL-17', as described herein above, refers to the protein also known as CTLA-8 or IL-17A.

In the method of the present invention the level of expression of LCN2 may be measured in any suitable test sample of a body fluid or tissue obtained from the subject. Suitable test samples include, but are not limited to, blood, serum, plasma, urine, tissue biopsy, stool, sputum, cerebrospinal fluid and bronchoalveolar lavage (BAL) fluid.

Suitable methods for determining the level of expression of LCN2 in a test sample are known in the art and these include, but are not limited to, immunoassays, gel electrophoresis followed by visualisation, detection of mRNA or measurement of LCN2 activity (e.g. iron shuttling, see for example Schmidt-Ott et al., J. Am. Soc. Nephrol. 2007, 18 (2) 407-413).

In one embodiment the level of expression of LCN2 is determined by measuring the level of LCN2 polypeptide in a test sample.

In one embodiment, the step of detecting the expression level of the LCN2 polypeptide comprises:
(a) contacting the test sample with a capture reagent that is specific for a LCN2 polypeptide; and
(b) detecting whether binding has occurred between the capture reagent and said LCN2 polypeptide in the sample.

In one aspect, the captured LCN2 polypeptide is detected using a directly or indirectly labelled detection reagent which may be immobilised on a solid phase.

A convenient means for detecting/quantifying a LCN2 polypeptide involves the use of antibodies. The LCN2 polypeptide can be detected by means of any immunoassay known in the art, including, without limitation, immunoprecipitation followed by sodium dodecyl sulfate polyacrylamide gel electrophoresis, 2 dimensional gel electrophoresis, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, immunoradiometric assays, fluorescent immunoassays and protein A immunoassays.

Detection of the interaction of an antibody with LCN2 can be facilitated by coupling the antibody to a detectable substance for example, but without limitation, an enzyme (such as horseradish peroxidase, alkaline phosphatase, beta-galactosidase, acetylcholinesterase), a prosthetic group (such as streptavidin, avidin, biotin), a fluorescent material (such as umbelliferone, fluorescein, fluorescein isothiocyanate, rhodamine, dichlorotriazinylamine fluorescein, dansyl chloride, phycoerythrin), a luminescent material (such as luminol), a bioluminescent material (such as luciferase, luciferin, aequorin), a radioactive nuclide (such as $^{125}$I, $^{131}$I, $^{111}$In, $^{99}$Tc) a positron emitting metal or a non-radioactive paramagnetic metal ion (see U.S. Pat. No. 4,741,900).

Examples of suitable assays for the detection of LCN2 are described by Xu et al., 1994, Journal of Immunological Methods, 171, 2, 245-252 and Flo et al., 2004, Nature 432, 917-921.

It will also be apparent to one skilled in the art that the level of expression of LCN2 may be determined by measuring the level of an LCN2 nucleic acid, preferably mRNA.

Nucleic acid detection may be achieved using any suitable method known in the art including for example, hybridisation assays, arrays of capture probes (mRNA or cDNA), amplification e.g. PCR, RT-PCR (see for example the methods described in WO2006/125105).

In the present invention the response of a subject to a medicament comprising an IL-17 inhibitor is monitored by measuring the level of expression of LCN2 in test samples obtained from the test subject before and after administration of said medicament. Preferably the level of expression of LCN2 is measured in samples taken over successive time intervals following administration of the medicament. For example LCN2 expression can be determined one or more times following administration of the medicament, e.g. over the course of therapy e.g. over the course of one, two, four, six weeks, six months or longer after initiating a therapeutic regimen.

SUMMARY OF THE INVENTION

In one embodiment of the present invention the levels of expression of lipocalin 2 in the subject before and after administration of a medicament comprising an IL-17 inhibitor are compared in order to determine the efficacy of the medicament. A decrease in the level of lipocalin 2 expression detected using the method of the present invention is indicative of a reduction in the level of IL-17 or IL-17 related physiological effects. In one embodiment therefore the level of LCN2 expression is reduced in response to treatment with an IL-17 inhibitor.

In the present invention, the subject may be suffering from any disorder mediated by IL-17 or associated with an increased level of IL-17 such as an autoimmune, inflammatory and/or neurologic disorder. Preferably, the pathological condition is selected from the group consisting of infections (viral, bacterial, fungal and parasitic), endotoxic shock associated with infection, arthritis, rheumatoid arthritis, asthma, pelvic inflammatory disease, Alzheimer's Disease, Crohn's disease, Ulcerative Colitis, Peyronie's Disease, coeliac disease, gallbladder disease, Pilonidal disease, peritonitis, psoriasis, vasculitis, surgical adhesions, stroke, Type I Diabetes, lyme arthritis, meningoencephalitis, immune mediated inflammatory disorders of the central and peripheral nervous system such as multiple sclerosis, systemic lupus erythematosus and Guillain-Barr syndrome, other autoimmune disorders, pancreatitis, trauma (surgery), graft-versus-host disease, transplant rejection, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, gastric cancer and colon cancer), heart disease including ischaemic diseases such as myocardial infarction as well as atherosclerosis, intravascular coagulation, bone resorption, osteoporosis, osteoarthritis, periodontitis and hypochlorhydia. In one embodiment the subject is suffering from a disorder selected from the group consisting of arthritis, rheumatoid arthritis, psoriasis, psoriatic arthritis, systemic onset juvenile idiopathic arthritis (JIA), systemic lupus erythematosus (SLE), multiple sclerosis, asthma, chronic obstructive airway disease, chronic obstructive pulmonary disease, atopic dermatitis, scleroderma, systemic sclerosis, lung fibrosis, Crohn's disease, ulcerative colitis and ankylosing spondylitis and other spondyloarthropathies.

In one embodiment the disorder is multiple sclerosis.
In one embodiment the disorder is rheumatoid arthritis.
In one embodiment the disorder is inflammatory bowel disease.
In one embodiment the disorder is Crohn's disease.
In one embodiment the disorder is ulcerative colitis.

Hence, in one embodiment the present invention provides a method of monitoring the response of a multiple-sclerosis patient to a medicament comprising an IL-17 inhibitor, wherein the level of expression of lipocalin 2 in a test sample of a body fluid or tissue obtained from the subject is assessed before and after administration of said medicament and wherein said level of expression of lipocalin 2 after administration of said medicament is compared to the level of expression of lipocalin 2 prior to administration of the medicament.

An inhibitor of IL-17 activity according to the present invention is an agent that interferes with the activity of IL-17. The term 'IL-17 activity' as used herein refers to the spectrum of activity understood in the art for IL-17 for example, the induction of secretion of IL-6 from fibroblasts by IL-17 (Yao et al., 1995, Journal of Immunology, 155, 5483-5486). Inhibitors according to the present invention may partially or completely inhibit IL-17 activity. Inhibitors of use in the present invention include without limitation, inhibitors that are capable of interacting with (e.g. binding to, or recognising) IL-17 or an IL-17 receptor (IL-17 RA or IL-17RC), or a nucleic acid molecule encoding IL-17 or IL-17R, or are capable of inhibiting the expression of IL-17 or IL-17 R or are capable of inhibiting the interaction between IL-17 and IL-17R. Such inhibitors may be, without limitation, antibodies, nucleic acids (e.g. DNA, RNA, antisense RNA and siRNA), carbohydrates, lipids, proteins, polypeptides, peptides, peptidomimetics, small molecules and other drugs.

Examples of suitable inhibitors include, but are not limited to, a synthetic functional fragment of an IL-17 receptor (IL-17RA or IL-17RC) that binds to IL-17 and interferes with binding to the native IL-17 receptor, an antibody that binds to IL-17 or to an IL-17 receptor and interferes with IL-17 receptor-ligand interaction, an antisense nucleic acid molecule that specifically hybridizes to mRNA encoding IL-17 or an IL-17 receptor or a small molecule or other drug which inhibits the activity of IL-17 or its receptor.

It will be appreciated that the IL-17 inhibitor for use in the present invention may be used alone or in combination with other therapeutic agents, and in the case of an antibody or antibody fragment, may be incorporated into other antibody formats, in particular, multi-specific antibody formats, such as bi or tri specific antibody formats, where one specificity is provided by an antibody of the present invention i.e. an inhibitor of IL-17A activity. Examples of multi-specific antibody formats include bi, tri or tetra-valent antibodies, Bis-scFv, diabodies, triabodies, tetrabodies, bibodies and tribodies (see for example Holliger and Hudson, 2005, Nature Biotech 23(9): 1126-1136; Schoonjans et a/0.2001, Biomolecular Engineering, 17 (6), 193-202). Other multi-specific antibody formats include Fab-Fv, Fab-dsFv, Fab-Fv-Fv. Fab-Fv-Fc and Fab-dsFv-PEG fragments described in WO2009040562, WO2010035012, WO2011/08609, WO2011/030107 and WO2011/061492 respectively.

Inhibitors of IL-17 activity are well known in the art as are methods of identifying and producing such inhibitors. Examples include, IL-17R:Fc and IL17RC-Fc fusion proteins (Lubberts et al., J. Immunol. 2001, 167, 1004-1013; Kuestner et al., J. Immunol. 2007, 179, 5462-5473 and WO2002058717) and neutralising antibodies (Chung et al., 2002, J. Exp. Med., 195, 1471-1478; Ferretti, 2003, Journal of Immunology, 170, 2106-2112; WO2006/054059, WO2006/013107, WO2007070750 and WO07149032). Suitable inhibitors of IL-17 activity also include IL-17A/F antibodies, i.e. antibodies which bind both IL-17A and IL-17F for example those described in WO2007/106769, WO2008/047134, WO2009/136286 and WO2010/025400.

Agents that may be suitable inhibitors can be selected from a wide variety of candidate agents. Examples of candidate agents include but are not limited to, nucleic acids (e.g. DNA and RNA), carbohydrates, lipids, proteins, polypeptides, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is suited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683).

Examples of suitable methods based on the present description for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented, for example, in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223, 409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

In one example, the inhibitor for use in the present invention may be a nucleic acid. In particular IL-17 or IL-17R nucleic acid molecules may be used as anti-sense molecules, to alter the expression of their respective polypeptides by binding to complementary nucleic acids. IL-17 or IL-17R nucleic acids may be obtained using standard cloning techniques from for example genomic DNA or cDNA or can be synthesised using well known and commercially available techniques. The IL-17 or IL-17R nucleic acids may contain one or more nucleotide substitutions, additions or deletions into the nucleotide sequence of an IL-17 or IL-17R nucleic acid. Standard techniques known to those of skill in the art can be used to introduce mutations, including, for example, site-directed mutagenesis and PCR-mediated mutagenesis. An antisense nucleic acid according to the present invention includes a IL-17 or IL-17R nucleic acid capable of hybridising by virtue of some sequence complementarity to a portion of an RNA (preferably mRNA) encoding the respective polypeptide. The antisense nucleic acid can be complementary to a coding and/or non-coding region of an mRNA encoding such a polypeptide. Most preferably, the antisense nucleic acids result in inhibition of the expression of the IL-17 or IL-17R polypeptide. Thus, in one embodiment the medicament comprising an IL-17 inhibitor comprises at least eight nucleotides that are anti-sense to a gene or cDNA encoding an IL-17 or IL-17R polypeptide.

In one example the IL-17 inhibitor comprises an IL-17R polypeptide or an IL-17 binding fragment thereof. In one embodiment the IL-17R polypeptide or IL-17 binding fragment thereof is an Fc fusion polypeptide (see for example WO2002058717). In one example the IL-17 inhibitor comprises an IL-17RC polypeptide or IL-17 binding fragment thereof. In one embodiment the IL-17RC polypeptide or IL-17 binding fragment thereof is an Fc fusion polypeptide (see for example Kuestner et al., J. Immunol. 2007, 179, 5462-5473).

Most preferably, an IL-17 inhibitor for use in the present invention is an antibody that interacts with (i.e. binds to or recognises) IL-17 or one or both of its receptors and inhibits the activity of IL-17.

In one example such antibodies selectively interact with IL-17. Selectively interacting with (e.g. recognising or binding to) means that the antibodies have a greater affinity for IL-17 polypeptides than for other polypeptides. Examples of suitable antibodies are those that inhibit the activity of IL-17 by binding to IL-17 in such a manner as to prevent it being biologically active, for example by preventing the binding of IL-17 to its receptor.

In another example the antibodies selectively interact with IL-17A and IL-17F. Selectively interacting with (e.g. recognising or binding to) means that the antibodies have a greater affinity for IL-17A and IL-17F polypeptides than for other polypeptides. Examples of suitable antibodies are those that inhibit the activity of IL-17 by binding to IL-17 in such a manner as to prevent it being biologically active, for example by preventing the binding of IL-17 to its receptor.

In another example the antibodies selectively interact with the IL-17 receptor. Selectively interacting with (e.g. recognising or binding to) means that the antibodies have a greater affinity for the IL-17 receptor polypeptide than for other polypeptides. Examples of suitable antibodies are those that inhibit the activity of IL-17 by preventing IL-17 mediated signalling from the receptor, for example by preventing IL-17 from binding to the IL-17 receptor.

Thus, in one embodiment the medicament comprising an IL-17 inhibitor for use in the present invention comprises an anti-IL-17 antibody or functionally active fragment thereof or an anti-IL-17R antibody or functionally active fragment thereof.

IL-17 or IL-17 receptor polypeptides or cells expressing said polypeptides can be used to produce antibodies which specifically recognise said polypeptides. The IL-17 and IL-17R polypeptides may be 'mature' polypeptides or biologically active fragments or derivatives thereof. IL-17 and IL-17 R polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. IL-17 or IL-17R polypeptides may in some instances be part of a larger protein such as a fusion protein for example fused to an affinity tag. Antibodies generated against these polypeptides may be obtained by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986. Many warm-blooded animals, such as rabbits, mice, rats, sheep, chickens, cows or pigs may be immunised. However, mice, rabbits, pigs and rats are generally preferred.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-7848 and in WO92/02551.

Humanized antibodies are antibody molecules from non-human species having one or more complementarity determining regions (CDRs) from the non-human species and a framework region from a human immunoglobulin molecule (see, e.g. U.S. Pat. No. 5,585,089). Humanized antibodies may optionally further comprise one or more framework residues derived from the non-human species from which the CDRs were derived.

Chimeric antibodies are those antibodies encoded by immunoglobulin genes that have been genetically engineered so that the light and heavy chain genes are composed of immunoglobulin gene segments belonging to different species. Bivalent antibodies may be made by methods known in the art (Milstein et al., 1983, Nature 305:537-539; WO 93/08829, Traunecker et al., 1991, EMBO J. 10:3655-3659). Multi-valent antibodies may comprise multiple specificities or may be monospecific (see for example WO 92/22853).

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat. No. 4,946,778 can also be adapted to produce single chain antibodies to IL-17 or IL-17R polypeptides. Also, transgenic mice, or other organisms, including other mammals, may be used to express humanized antibodies.

Anti-IL-17 and anti-IL-17 receptor antibodies for use in the present invention include whole antibodies and functionally active fragments or derivatives thereof and may be, but are not limited to, polyclonal, monoclonal, multi-valent, multi-specific, humanized or chimeric antibodies, single chain antibodies, Fab fragments, Fab' and F(ab')$_2$ fragments, fragments produced by a Fab expression library and epitope-binding fragments of any of the above. Antibodies include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD and IgA) or subclass of immunoglobulin molecule.

Antibody fragments and methods of producing them are well known in the art, see for example Verma et al., 1998, Journal of Immunological Methods, 216, 165-181. Particular examples of antibody fragments for use in the present invention are Fab' fragments which possess a native or a modified hinge region. A number of modified hinge regions have already been described, for example, in U.S. Pat. No. 5,677,425, WO9915549, and WO9825971 and these are incorporated herein by reference.

If desired an antibody for use in the present invention may be conjugated to one or more effector molecule(s). The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy. In one example, anti-IL-17 or anti IL-17 R antibodies can be conjugated to an effector molecule, such as a cytotoxic agent, a radionuclide, a peptide or polypeptide, or drug moiety to modify a given biological response. In another example the effector molecule may increase half-life in vivo, and/or decrease immunogenicity and/or enhance the delivery of an antibody across an epithelial barrier to the immune system. Examples of suitable effector molecules include polymers and proteins such as albumin and albumin binding proteins. Examples of suitable polymers include any synthetic or naturally occurring substantially water-soluble, substantially non-antigenic polymer including, for example, optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen. Particular optional substituents which may be present on the above-mentioned synthetic polymers include one or more hydroxy, methyl or methoxy groups. Particular examples of synthetic polymers include optionally substituted straight or branched chain poly(ethyleneglycol), poly (propyleneglycol), poly(vinylalcohol) or derivatives thereof, especially optionally substituted poly(ethyleneglycol) such as methoxypoly(ethyleneglycol). Preferably the polymer is a polyalkylene oxide such as polyethylene glycol (PEG).

In another embodiment the present invention provides a method of stratifying patients (i.e., selecting individuals with a probable diagnosis of cancer and/or an autoimmune, and/or inflammatory and/or neurologic disorder or diagnosed with cancer and/or an autoimmune and/or inflammatory and/or neurologic disorder for treatment with an IL-17 inhibitor) by obtaining measurements of the level of expression of lipocalin 2 in a test sample from such patients. The measured level of lipocalin 2 is compared with a reference value, such as a reference subject, sample or cohort e.g. from a 'normal' or 'healthy' subject or population of subjects. In one example the reference value is the average level of lipocalin 2 determined in a plurality of isolated samples from healthy individuals. Those subjects exhibiting elevated levels of lipocalin 2 are deemed suitable for treatment with an IL-17 inhibitor.

The information thus obtained may be used to aid in stratification of the diagnosis (or probable diagnosis) of the individual. Accordingly, in one embodiment the present invention provides a method for selecting a patient suitable for treatment with a medicament comprising an IL-17 inhibitor and treating said patient with said medicament, the method comprising:

(1) comparing a measured level of lipocalin 2 expression in a test sample of a body fluid or tissue obtained from said patient with a reference value for lipocalin 2 expression and (2) if elevated compared to the reference value, initiating therapy with a medicament comprising an IL-17 inhibitor.

The present invention also provides the use of an IL-17 inhibitor in the manufacture of a medicament for the treatment of an IL-17 mediated disease wherein the patient is selected by comparing the level of lipocalin 2 expression in a test sample of a body fluid or tissue from said patient to a reference value. It will be appreciated that the patient will only be treated using a medicament comprising an IL-17 inhibitor if the level of lipocalin 2 expression in the patient is higher than the reference value.

Similarly, also provided is an IL-17 inhibitor for use in the treatment of an IL-17 mediated disease wherein the patient is selected by comparing the level of lipocalin 2 expression in a test sample of a body fluid or tissue from said patient to a reference value.

Furthermore, the level of expression of lipocalin 2 may be used to determine a suitable dose of a medicament comprising an IL-17 inhibitor to be administered to the individual, for example by comparing the measured level of expression of lipocalin 2 in the individual to one or more reference values of lipocalin 2 each associated with a particular dose of a medicament comprising an IL-17 inhibitor. Hence in one embodiment the present invention provides a method of selecting a suitable dose of a medicament comprising an IL-17 inhibitor for use in the treatment of a patient known to have elevated levels of lipocalin 2 expression said method comprising:

(a) comparing the measured level for lipocalin 2 expression in a test sample of a body fluid or tissue from said patient to at least one reference value of lipocalin 2 expression and (b) selecting a suitable dose of a medicament comprising an IL-17 inhibitor based on the comparison made in step (a).

It will be appreciated that this method may further comprise an additional step (c) initiating therapy with a medicament comprising an IL-17 inhibitor at the dose selected in step (b).

The present invention also provides the use of an IL-17 inhibitor in the manufacture of a medicament for the treatment of an IL-17 mediated disease wherein the dose of IL-17 inhibitor is selected by comparing the level of lipocalin 2 expression in a test sample of a body fluid or tissue from the patient to a reference value.

Also provided is an IL-17 inhibitor for use in the treatment of an IL-17 mediated disease wherein the dose of IL-17 inhibitor is selected by comparing the level of lipocalin 2 expression in a test sample of a body fluid or tissue from the patient to a reference value.

Inhibitors of IL-17 activity used in the treatment and/or prophylaxis of IL-17 mediated disease will generally be administered in the form of a pharmaceutical composition typically comprising a pharmaceutically acceptable carrier.

The term 'treatment' includes either therapeutic or prophylactic therapy. When a reference is made herein to a method of treating or preventing a disease or condition using a particular inhibitor or combination of inhibitors, it is to be understood that such a reference is intended to include the use of that inhibitor or combination of inhibitors for the manufacture of a medicament for the treatment and/or prophylaxis of an IL-17 mediated or associated condition such as multiple sclerosis.

The composition will usually be supplied as part of a sterile, pharmaceutical composition that will normally include a pharmaceutically acceptable carrier. This composition may be in any suitable form (depending upon the desired method of administering it to a patient).

The inhibitors of use in the invention are preferably administered to a subject by a variety of other routes such as orally, transdermally, subcutaneously, intranasally, intravenously, intramuscularly, intrathecally and intracerebroventricularly. The most suitable route for administration in any given case will depend on the particular inhibitor, the subject, and the nature and severity of the disease and the physical condition of the subject.

The inhibitors of use in the invention may be administered in combination, e.g. simultaneously, sequentially or separately, with one or more other therapeutically active compounds, which may be for example other anti-MS therapies or anti-cancer therapies.

Pharmaceutical compositions may be conveniently presented in unit dose forms containing a predetermined amount of an active agent of the invention per dose. Such a unit may contain for example but without limitation, 750 mg/kg to 0.1 mg/kg depending on the condition being treated, the route of administration and the age, weight and condition of the subject.

Pharmaceutically acceptable carriers for use in the invention may take a wide variety of forms depending, e.g. on the route of administration.

Compositions for oral administration may be liquid or solid. Oral liquid preparations may be in the form of, for example, aqueous or oily suspensions, solutions, emulsions, syrups or elixirs, or may be presented as a dry product for reconstitution with water or other suitable vehicle before use. Oral liquid preparations may contain suspending agents as known in the art.

In the case of oral solid preparations such as powders, capsules and tablets, carriers such as starches, sugars, microcrystalline cellulose, granulating agents, lubricants, binders, disintegrating agents, and the like may be included. Because of their ease of administration, tablets and capsules represent the most advantageous oral dosage unit form in which case solid pharmaceutical carriers are generally employed. In addition to the common dosage forms set out above, active agents of the invention may also be administered by controlled release means and/or delivery devices. Tablets and capsules may comprise conventional carriers or excipients such as binding agents for example, syrup, acacia, gelatin, sorbitol, tragacanth, or polyvinylpyrrolidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulphate. The tablets may be coated by standard aqueous or non-aqueous techniques according to methods well known in normal pharmaceutical practice.

Pharmaceutical compositions of the present invention suitable for oral administration may be presented as discrete units such as capsules, cachets or tablets, each containing a predetermined amount of the active agent, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active agent with the carrier, which constitutes one or more necessary ingredients. In general, the compositions are prepared by uniformly and intimately admixing the active agent with liquid carriers or finely divided solid carriers or both, and then, if necessary, shaping the product into the desired presentation. For example, a tablet may be prepared by compression or moulding, optionally with one or more accessory ingredients.

Pharmaceutical compositions suitable for parenteral administration may be prepared as solutions or suspensions of the active agents of the invention in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include aqueous or non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. Extemporaneous injection solutions, dispersions and suspensions may be prepared from sterile powders, granules and tablets.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollients in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base. Alternatively, the active agent may be formulated in a cream with an oil-in-water cream base or a water-in-oil base.

Pharmaceutical compositions adapted for topical administration in the mouth include lozenges, pastilles and mouth washes.

Pharmaceutical compositions adapted for topical administration to the eye include eye drops wherein the active agent is dissolved or suspended in a suitable carrier, especially an aqueous solvent. They also include topical ointments or creams as above.

Pharmaceutical compositions suitable for rectal administration wherein the carrier is a solid are most preferably presented as unit dose suppositories. Suitable carriers include cocoa butter or other glyceride or materials commonly used in the art, and the suppositories may be conveniently formed by admixture of the combination with the softened or melted carrier(s) followed by chilling and shaping moulds. They may also be administered as enemas.

The dosage to be administered of an inhibitor of IL-17 activity will vary according to the particular inhibitor, the type of disease, the subject, and the nature and severity of the disease and the physical condition of the subject, and the selected route of administration; the appropriate dosage can be readily determined by a person skilled in the art. For the treatment and/or prophylaxis of disease in humans and animals pharmaceutical compositions comprising antibodies can be administered to patients (e.g., human subjects) at therapeutically or prophylactically effective dosages (e.g. dosages which result in inhibition of disease and/or relief of disease symptoms) using any suitable route of administration, such as injection and other routes of administration known in the art for clinical products, such as antibody-based clinical products.

The compositions may contain from 0.1% by weight, preferably from 10-60%, or more, by weight, of the inhibitor of the invention, depending on the method of administration.

It will be recognized by one of skill in the art that the optimal quantity and spacing of individual dosages of an inhibitor of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

In another example, where the inhibitor is a nucleic acid this may be administered via gene therapy (see for example Hoshida, T. et al., 2002, Pancreas, 25:111-121; Ikuno, Y. 2002, Invest. Ophthalmol. Vis. Sci. 2002 43:2406-2411; Bollard, C., 2002, Blood 99:3179-3187; Lee E., 2001, Mol. Med. 7:773-782). Gene therapy refers to administration to a subject of an expressed or expressible nucleic acid. In one example this is either the IL-17 or the IL-17R nucleic acid or portions thereof. Any of the methods for gene therapy available in the art can be used according to the present invention.

Delivery of the therapeutic nucleic acid into a patient can be direct in vivo gene therapy (i.e. the patient is directly exposed to the nucleic acid or nucleic acid-containing vector) or indirect ex vivo gene therapy (i.e. cells are first transformed with the nucleic acid in vitro and then transplanted into the patient).

For example for in vivo gene therapy, an expression vector containing the IL-17 or IL-17R nucleic acid may be administered in such a manner that it becomes intracellular, i.e. by infection using a defective or attenuated retroviral or other viral vectors as described, for example, in U.S. Pat. No. 4,980,286 or by Robbins et al., 1998, Pharmacol. Ther. 80:35-47.

The various retroviral vectors that are known in the art are such as those described in Miller et al. (1993, Meth. Enzymol. 217:581-599) which have been modified to delete those retroviral sequences which are not required for packaging of the viral genome and subsequent integration into host cell DNA. Also adenoviral vectors can be used which are advantageous due to their ability to infect non-dividing cells and such high-capacity adenoviral vectors are described in Kochanek (1999, Human Gene Therapy, 10:2451-2459). Chimeric viral vectors that can be used are those described by Reynolds et al. (1999, Molecular Medicine Today, 1:25-31). Hybrid vectors can also be used and are described by Jacoby et al. (1997, Gene Therapy, 4:1282-1283).

Direct injection of naked DNA or through the use of microparticle bombardment (e.g. Gene Gun®; Biolistic, Dupont) or by coating it with lipids can also be used in gene therapy. Cell-surface receptors/transfecting compounds or through encapsulation in liposomes, microparticles or microcapsules or by administering the nucleic acid in linkage to a peptide which is known to enter the nucleus or by administering it in linkage to a ligand predisposed to receptor-mediated endocytosis (See Wu & Wu, 1987, J. Biol. Chem., 262:4429-4432) can be used to target cell types which specifically express the receptors of interest.

In ex vivo gene therapy, a gene is transferred into cells in vitro using tissue culture and the cells are delivered to the patient by various methods such as injecting subcutaneously, application of the cells into a skin graft and the intravenous injection of recombinant blood cells such as haematopoietic stem or progenitor cells.

Cells into which a IL-17 or IL-17R nucleic acid can be introduced for the purposes of gene therapy include, for example, epithelial cells, endothelial cells, keratinocytes, fibroblasts, muscle cells, hepatocytes and blood cells. The blood cells that can be used include, for example, T-lymphocytes, B-lymphocytes, monocytes, macrophages, neutrophils, eosinophils, megakaryocytes, granulocytes, haematopoietic cells or progenitor cells, and the like.

In a one aspect, the pharmaceutical composition of the present invention comprises an IL-17 or IL-17R nucleic acid, said nucleic acid being part of an expression vector that expresses an IL-17 or IL-17R polypeptide or chimeric protein thereof in a suitable host. In particular, such a nucleic acid has a promoter operably linked to the polypeptide coding region, said promoter being inducible or constitutive (and, optionally, tissue-specific).

The invention will now be described with reference to the following examples, which are merely illustrative and should not in any way be construed as limiting the scope of the present invention.

DETAILED DESCRIPTION OF THE INVENTION

Examples

Figure 1:
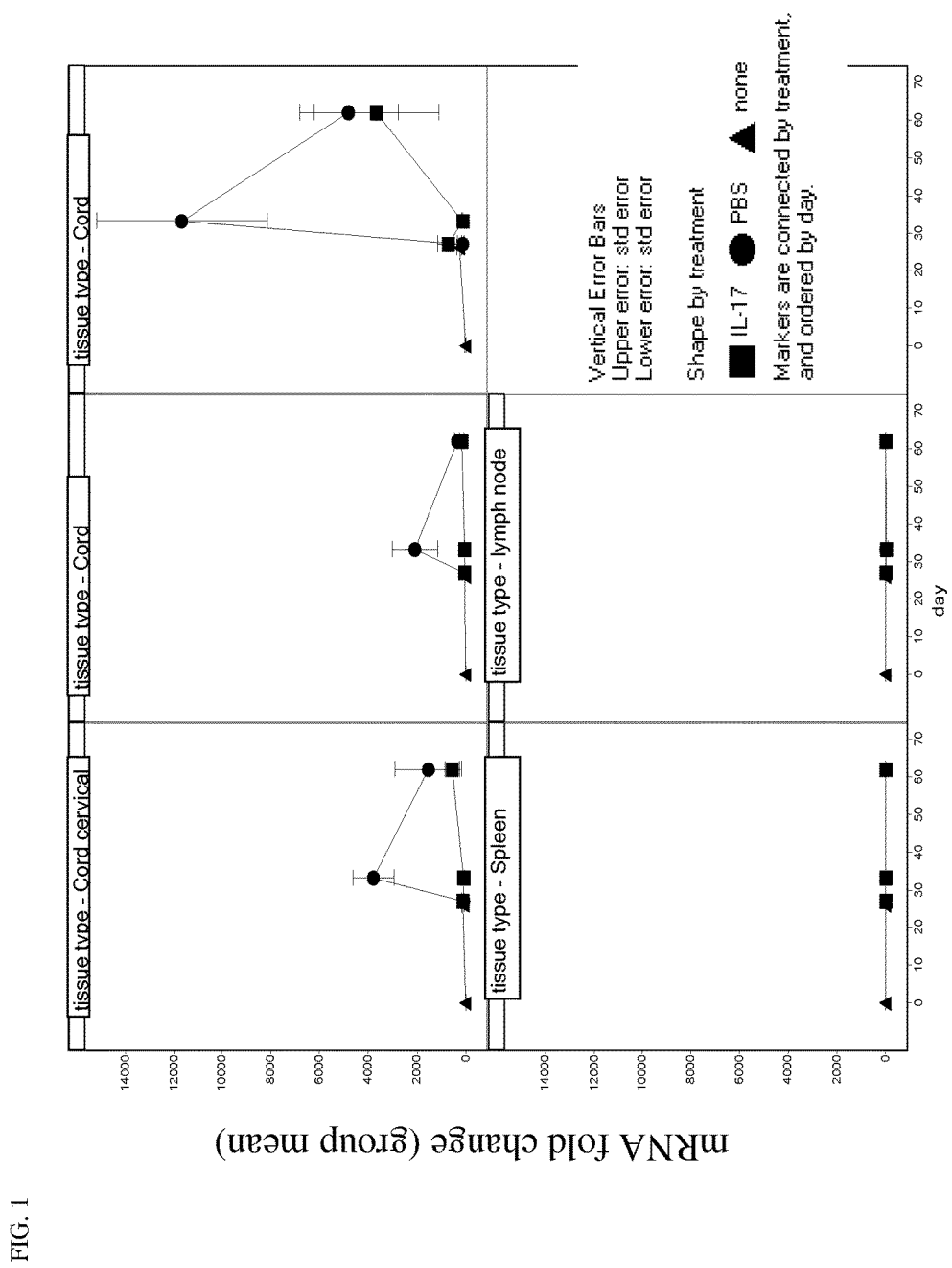
FIG. 1: Data from LCN2 gene expression analysis in five tissues (Cord cervical, Cord Lumbar, Cord Thoracic, Spleen, Lymph node) from an EAE mouse model, both control (PBS) and following treatment with an anti-IL-17 antibody.

Example 1. Effect of Anti-IL-17 Antibody on LCN2 Gene Expression in Murine Model of MS (EAE)

The anti-murine IL-17 antibody used in these experiments was Ab#13 IgG1 as described previously in WO05/051422.

The MS model, experimental autoimmune encephalomyelitis (EAE), was used essentially as described by Baker et al., 1990. Journal of Neuroimmunology, 28:261-270.

Female ABH mice 8-10 weeks of age (Harlan) were immunised with mouse spinal cord homogenate (SCH, 3.33 mg/ml) in complete freund's adjuvant by subcutaneous immunisation in either flank (150 µl/site) on PSD0 and PSD7.

i) Dosing Over the Acute Phase

Two groups were dosed with antibody at 10 mg/kg, sc on PSD-1, PSD6, PSD13 and PSD20 (1× weekly). One group (n=14) was dosed with Ab#13 mIgG1 the other (n=13) with PBS.

ii) Dosing Over the Relapsing Phase

A total of 30 mice were followed through the acute phase of disease and on PSD27 analysis of the acute phase of disease was performed to select two groups with similar disease profiles in the acute phase (day of onset, peak disease score, cumulative clinical score and weight loss). Two groups of 12 mice were selected for dosing with antibody at 10 mg/kg, sc on PSD28, PSD35, PSD42 and PSD49. One group was dosed with Ab#13 mIgG1 the other with PBS.

Weights and clinical scores were recorded daily by an assessor blinded to treatment and terminal EDTA-Plasma collected.

Clinical Score Scale

| | |
|---|---|
| 0 | Normal |
| 0.25 | Tail dragging |
| 0.5 | Partial tail paralysis |
| 1 | Complete tail paralysis |
| 2 | Incomplete hind limb paralysis |
| 3 | Complete hind paralysis/incontinence |
| 4 | Front limb paralysis/loss of righting reflex |

Statistics

Pairwise comparisons of clinical scores and day of onset were performed using Mann-Whitney U test, analysis of incidence was performed with Fishers exact test, analysis of maximum weight loss was performed using Students' T test.

Tissue samples were taken from five different tissues (Cord cervical, Cord Lumbar, Cord Thoracic, Spleen, Lymph node) at three different time points PSD26 for naïve group, PSD27, PSD33 and PSD62 for PBS and anti-IL-17 groups.

LCN2 gene expression in tissue samples from the EAE mouse model was determined using TaqMan® (Applied Biosystems. Probe Mm.00809552).

cDNA Synthesis (Reverse Transcription) and Real time PCR 75 ng of total RNA from each of the tissue samples were used in the reverse transcription (RT) reaction. The RT reaction was performed as per protocol using TaqMan® RT reagents (Applied Biosystems) using the Gene Amp PCR System 9700 at 25° C.×10 min, 37° C.×60 min, 95° C.×5 min, 4° C. hold.

cDNA from each RT reaction were used in the Real Time PCR using custom designed TaqMan® Low Density Array (LDA) cards using the Applied Biosystems 7900 HT Fast Real Time PCR system.

For Each LDA Port Mix:

| | |
|---|---|
| cDNA sample | 20 ul |
| RNase/DNase-free water | 30 ul |
| TaqMan Universal PCR Master Mix (2x) | 50 ul |
| Total | 100 ul |

The probe for Lipocalin 2 used was Applied Biosystems Probe Mm00809552_s1

Reaction conditions were 50° C.×2 min, 94.5° C.×10 min, (97° C.×30 sec and 59.7° C.×1 min)×40 cycles The Real Time PCR data was analysed using CT values obtained from the ABI software SDS 2.1 using automatic threshold and baseline.

18S rRNA gene (ABI probe Hs99999901_s1) was used as endogenous/housekeeper gene to normalize the CT values to the amount of cDNA present in each well (ΔCT value).

The gene fold changes were then calculated using the Comparative CT Method of relative quantification (de Kok et al., Real-time quantification of human telomerase reverse transcriptasemRNA in tumors and healthy tissues. *Clin. Chem.* 2000. March; 46(3):313-8).). The calibrator value used in this experiment to calculate the ΔΔCT was the mean of the ΔCT values of the naive samples per each tissue type. The relative quantity (or fold change) was calculated using the formula:

$$2^{-\Delta\Delta CT}.$$

Gene expression analysis of 5 tissue samples (Cord cervical, Cord Lumbar, Cord Thoracic, Spleen, Lymph node) from the EAE mouse model described above highlighted a significant upregulation of the LCN2 gene at PSD33 in spinal cord samples. This expression was reduced to baseline levels by treatment with an anti-IL-17 antibody (FIG. 1).

| | Unpaired t test at day 33 PBS vs anti-IL17 | | |
|---|---|---|---|
| | Cervical | Thoracic | Lumbar |
| P value | P < 0.0001 | P < 0.0001 | P < 0.0001 |
| P value summary | *** | *** | *** |
| Are means signif. different? (P < 0.05) | Yes | Yes | Yes |

Example 2. Effect of Anti-IL-17 Antibody on LCN2 Protein Levels in Mouse Plasma/Serum in EAE The EAE model and anti-IL-17 antibody were as described in Example 1. Antibody was used at 10 mg/kg s.c. 1× weekly from PSD48 as previously described in Example 1 (ii).

Figure 2:
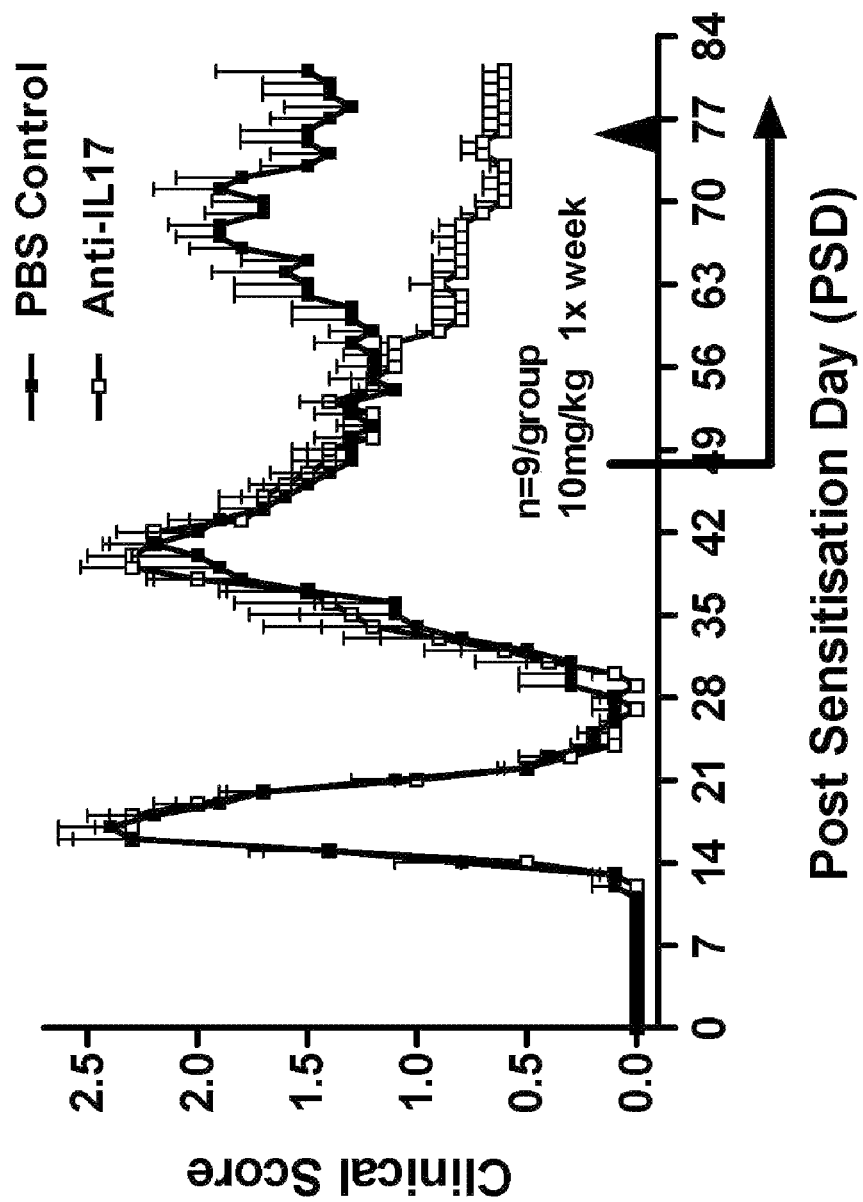
FIG. 2: Effect of Ab#13 mIgG1 on clinical disease when dosed through the $2^{nd}$ relapse phase. Average clinical score (+/−SEM) plotted against days post adjuvant immunisation (Post Sensitisation Day, PSD). Time point of sample indicated by black arrowhead.

Plasma samples were taken at relapse-2 (in controls) whilst the anti-IL-17 treated animals were largely asymptomatic. Exact sampling timepoint occurred as the controls reached chronicity so ranges from PSD 72-82 (with most occurring between PSD 80-82), as indicated by the arrow in FIG. 2.

Plasma samples taken at relapse-2 were tested for the presence of LCN2 protein using the protocol described below.

MSD Assay for Measurement of Mouse Lcn2

R&D Reagents Used:
  anti-mLcn2 monoclonal Ab raised in rat (cat.#MAB 1857) used for capture (coating) (stock solution is 500 ug/ml in PBS)
  anti-mLcn2 polyclonal Ab raised in goat (cat.#AF1857) used as "primary" (stock solution is 200 ug/ml in PBS)
  recombinant mouse Lcn2, CF (cat#1857-LC) used as control MSD Antibody Used:
  anti-goat IgG SULFOTAGGED raised in donkey (cat. #R32AG-5) detection antibody The MSD assay was set up according to the following protocol:

Coating:
A High-Bind MSD large spot plate was spotted with 5 ul per well of the capture (monoclonal) antibody at 100 ug/ml in PBS (FAC=500 ng/well). E.g. 100 ul stock in 400 ul PBS for one plate and the plate was left to dry for 90 minutes in a laminar flow hood. The plate was washed three times with 150 ul per well of PBS+0.05% Tween 20.

Blocking.
A solution of 3% MSD blocker A and 1% MSD blocker B in PBS+0.05% Tween 20 was prepared for use as a blocking agent. 150 ul of blocking buffer was added to all wells of the coated plate and the plate was incubated for 45 minutes at room temperature with vigorous shaking. The plate was then washed three times with PBS-Tween.

Binding:
Control: a standard curve was prepared using rmLcn2 from 40,000 pg down to 9.76 pg/well.

Sample: Optimum dilution of plasma and urine samples was determined (⅕ to ¹⁄₁₀₀ recommended) in PBS-tween and 25 ul/well was loaded. The plate was incubated for 2 hours at room temperature with shaking before being washed three times with PBS-Tween.

Primary:
Polyclonal antibody anti-mLcn2 raised in goat (R&D cat.#AF1857) at 4 ug/ml in PBS-T was added at 25 ul/well (=100 ng/ml) before being washed three times with PBS-Tween.

Secondary:
MSD anti-goat IgG SULFOTAGGED was prepared at 1 ug/ml in PBS+1% BSA. 25 ul of SULFOTAG reagent was added to all wells and the plate was incubated for 1 hour at room temperature with shaking. Plate was then washed three times with PBS-Tween.

Detection:
150 ul of MSD Read Buffer T at 1× concentration was added to all wells and the plate was read immediately on the SectorImager 6000

Figure 3:
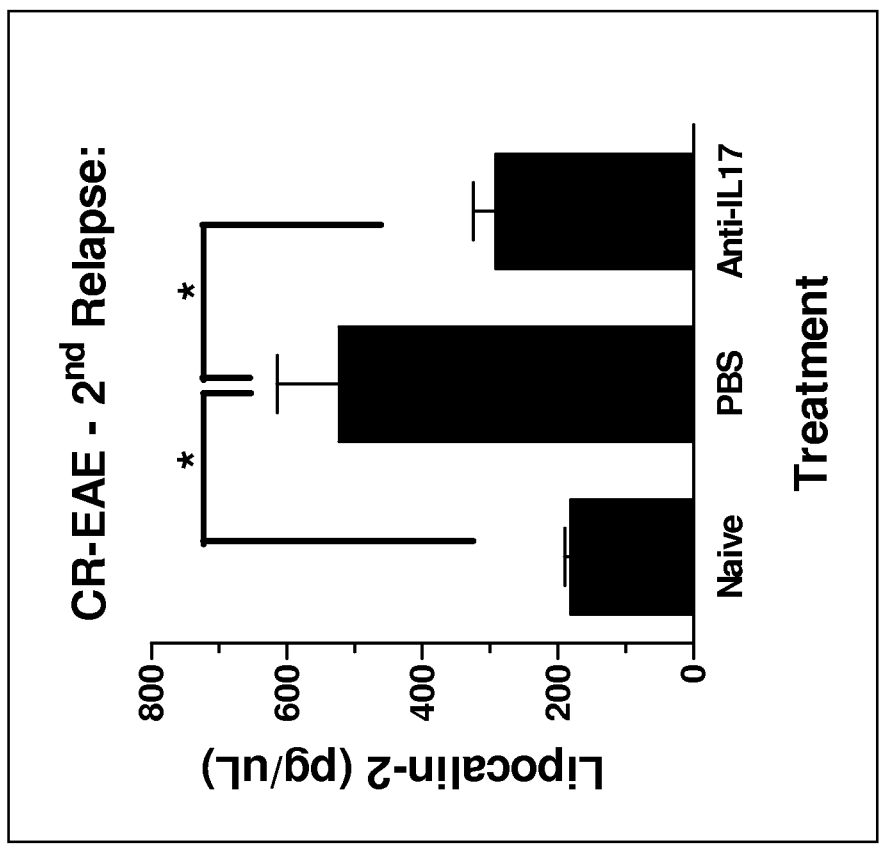
FIG. 3: LCN2 protein levels in plasma samples from an EAE mouse model ($2^{nd}$ relapse), in both control (PBS) and following treatment with an anti-IL-17 antibody.

Results
LCN2 protein levels were increased in the diseased group and modulated with statistical significance by anti-IL-17 antibody (See FIG. 3). *=p<0.05 ANOVA with Bonferronis multiple corrections. Naives were age matched.

An publications mentioned in the above specification are herein incorporated by reference.

Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry, molecular biology and biotechnology or related fields are intended to be within the scope of the following claims.

What is claimed is:

1. A method for monitoring the effect of a medicament for treating a disease mediated by increased levels of IL-17A comprising:
   (a) administering a medicament comprising an anti-IL-17A/F antibody to a subject suffering from a disease mediated by increased levels of IL-17A;
   (b) measuring the level of mRNA expression of lipocalin 2 or the level of lipocalin 2 protein in a test sample of body fluid or tissue obtained from the subject and detecting a decrease in the level of mRNA expression of lipocalin 2 or the level of lipocalin 2 protein compared to the level of mRNA expression of lipocalin 2 or the level of lipocalin 2 protein prior to administration of the medicament; and
   (c) administering at least one additional dose of the medicament comprising the anti-IL-17A/F antibody to the subject.

2. The method according to claim 1 wherein the subject is suffering from a disorder selected from the group consisting of arthritis, rheumatoid arthritis, psoriasis, psoriatic arthritis, systemic onset juvenile idiopathic arthritis (JIA), systemic lupus erythematosus (SLE), multiple sclerosis, asthma, chronic obstructive airway disease, chronic obstructive pulmonary disease, atopic dermatitis, scleroderma, systemic sclerosis, lung fibrosis, Crohn's disease, ulcerative colitis and ankylosing spondylitis and other spondyloarthropathies.

3. The method according to claim 1 wherein the subject is suffering from an autoimmune disorder.

4. The method according to claim 1 or 3 wherein the test sample is selected from blood, serum, plasma, urine, tissue biopsy, stool, sputum, cerebrospinal fluid and bronchioalveolar lavage fluid.

5. The method according to claim 3, wherein the subject is suffering from multiple sclerosis, rheumatoid arthritis, psoriasis, psoriatic arthritis, systemic onset juvenile idiopathic arthritis (JIA), or systemic lupus erythematosus (SLE).

6. A method for treating an IL-17 mediated disease in a patient comprising administering an effective dose of an IL-17 inhibitor to said patient, wherein the effective dose is determined by (a) comparing the level of lipocalin 2 expression in a test sample of a body fluid or tissue from said patient to a reference value; and (b) selecting a suitable dose of a medicament comprising an IL-17 inhibitor based on the comparison made in step (a).

* * * * *

UNITED STATES PATENT AND TRADEMARK OFFICE
CERTIFICATE OF CORRECTION

Page 1 of 1

PATENT NO. : 10,208,349 B2
APPLICATION NO. : 14/084047
DATED : February 19, 2019
INVENTOR(S) : Adam Samuel Platt et al.

It is certified that error appears in the above-identified patent and that said Letters Patent is hereby corrected as shown below:

On the Title Page

(72) Inventors:
"GILLIAN SAIRFULL WATT, LUTON (GB)"

Should be replaced with:
--GILLIAN FAIRFULL WATT, LUTON (GB)--

Signed and Sealed this
Thirtieth Day of April, 2019

Andrei Iancu
*Director of the United States Patent and Trademark Office*